(12) United States Patent
Sohrab

(10) Patent No.: US 6,501,976 B1
(45) Date of Patent: Dec. 31, 2002

(54) PERCUTANEOUS BIOLOGICAL FLUID SAMPLING AND ANALYTE MEASUREMENT DEVICES AND METHODS

(75) Inventor: Borzu Sohrab, Los Altos, CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 09/879,106

(22) Filed: Jun. 12, 2001

(51) Int. Cl.7 .............................. A61B 5/65; A61B 5/00; A61B 5/04

(52) U.S. Cl. ...................... 600/347; 600/345; 600/365; 600/393

(58) Field of Search ................................. 600/347, 345, 600/346, 348, 352, 353, 354, 355, 357, 358, 365, 366, 372, 373, 377, 393

(56) References Cited

U.S. PATENT DOCUMENTS

| | | | |
|---|---|---|---|
| 3,682,162 A | * 8/1972 | Colyer | ......................... 600/373 |
| 5,161,532 A | 11/1992 | Joseph | |
| 5,582,184 A | 12/1996 | Erickson et al. | |
| 5,746,217 A | 5/1998 | Erickson et al. | |
| 5,879,310 A | 3/1999 | Sopp et al. | |
| 5,879,367 A | 3/1999 | Latterell et al. | |
| 5,942,102 A | 8/1999 | Hodges et al. | |
| 6,080,116 A | 6/2000 | Erickson et al. | |
| 6,083,196 A | 7/2000 | Trautman et al. | |
| 6,091,975 A | 7/2000 | Daddona et al. | |
| 6,139,718 A | * 10/2000 | Kurnik et al. | ........ 204/403.14 |
| 6,162,611 A | 12/2000 | Heller et al. | |
| 6,248,067 B1 | * 6/2001 | Causey et al. | .............. 128/903 |
| 6,360,888 B1 | * 3/2002 | McIvor et al. | .............. 206/305 |

FOREIGN PATENT DOCUMENTS

| | | |
|---|---|---|
| WO | WO 97/00441 | 1/1997 |
| WO | WO 97/42888 | 11/1997 |
| WO | WO 98/00193 | 1/1998 |
| WO | WO 908/34541 | 8/1998 |
| WO | WO 99/13336 | 3/1999 |
| WO | WO 99/27852 | 6/1999 |
| WO | WO 99/64580 | 12/1999 |
| WO | WO 00/35530 | 6/2000 |
| WO | WO 00/45708 | 8/2000 |
| WO | WO 00/57177 | 9/2000 |
| WO | WO 00/74763 | 12/2000 |
| WO | WO 00/74765 | 12/2000 |

* cited by examiner

Primary Examiner—Kevin Shaver
Assistant Examiner—Navin Natnithithadha

(57) ABSTRACT

Devices and methods for sampling a biological fluid and measuring a target constituent within the biological fluid are provided. Generally, the subject devices include a sampling device configured to pierce a skin surface to provide access to biological fluid and concentrically-spaced working and reference electrodes positioned within the elongated sampling device that define an electrochemical cell for measuring the concentration of analyte within the biological fluid. The subject devices and methods are particularly suited for use in the sampling and concentration measuring of glucose in interstitial fluids. Also provided are kits that include the subject devices for use in practicing the subject methods.

33 Claims, 4 Drawing Sheets

PERCUTANEOUS BIOLOGICAL FLUID SAMPLING AND ANALYTE MEASUREMENT DEVICES AND METHODS

FIELD OF THE INVENTION

This field of this invention is minimally invasive biological fluid sampling and analyte measurement devices.

BACKGROUND

The detection of analytes in biological fluids is of ever increasing importance. Analyte detection assays find use in a variety of applications, including clinical laboratory testing, home testing, etc., where the results of such testing play a prominent role in the diagnosis and management of a variety of disease conditions. Common analytes of interest include glucose, e.g., for diabetes management, cholesterol, and the like.

A common technique for collecting a sample of blood for analyte determination is to pierce the skin at least into the subcutaneous layer to access the underlining blood vessels in order to produce localized bleeding on the body surface. The accessed blood is then collected into a small tube for delivery and analyzed by testing equipment, often in the form of a hand-held instrument having a reagent test strip onto which the blood sample is placed. The fingertip is the most frequently used site for this method of blood collection due to the large number of small blood vessels located therein. This method has the significant disadvantage of being very painful because subcutaneous tissue of the fingertip has a large concentration of nerve endings. It is not uncommon for patients who require frequent monitoring of an analyte to avoid having their blood sampled. With diabetics, for example, the failure to frequently measure their glucose level on a prescribed basis results in a lack of information necessary to properly control the level of glucose. Uncontrolled glucose levels can be very dangerous and even life-threatening. This technique of blood sampling also runs the risk of infection and the transmission of disease to the patient, particularly when done on a high-frequency basis. The problems with this technique are exacerbated by the fact that there is a limited amount of skin surface that can be used for the frequent sampling of blood.

To overcome the disadvantages of the above technique and others that are associated with a high degree of pain, certain analyte detection protocols and devices have been developed that use micro-needles or analogous structures to access the interstitial fluid within the skin. The micro-needles are penetrated into the skin to a depth less than the subcutaneous layer so as to minimize the pain felt by the patient. The interstitial fluid is then sampled and tested to determine the concentration of the target constituent. The concentration of a constituent within the interstitial fluid is representative of the concentration of that constituent in other bodily fluids, such as blood. Thus, by sampling interstitial fluid and measuring the level of glucose therein, for example, the corresponding level of glucose in the patient's blood can be derived.

Despite the work that has already been done in the area of analyte testing, there is a continued interest in the identification of new analyte detection methods that more readily meet the needs of the relevant market. Of particular interest would be the development of a minimally invasive analyte detection system that is practical, manufacturable, accurate, easy to use, as well as safe and efficacious.

RELEVANT LITERATURE

U.S. Patents of interest include: U.S. Pat. Nos. 5,161,532, 5,582,184, 5,746,217, 5,820,570, 5,879,310, 5,879,367, 5,942,102, 6,080,116, 6,083,196, 6,091,975 and 6,162,611. Other patent documents and publications of interest include: WO 97/00441, WO 97/42888, WO 98/00193 WO 98/34541, WO 99/13336, WO 99/27852, WO 99/64580, WO 00/35530, WO 00/45708, WO 00/57177, WO 00/74763 and WO 00/74765A1.

SUMMARY OF THE INVENTION

Minimally invasive biological fluid sampling and analyte measurement devices and systems, as well as methods for using the same, are provided. Generally, the subject device includes an elongated sampling means configured to pierce a skin surface to provide access to biological fluid, and concentrically-spaced working and reference electrodes positioned within the elongated sampling means that define an electrochemical cell for measuring the concentration of analyte within the biological fluid. In certain embodiments, the device further includes an insulating material positioned between the concentrically-spaced electrodes. The device also includes means for making an electrochemical measurement of an analyte in the electrochemical cell, e.g., a coulometric, amperometric or potentiometric measurement.

In a more specific embodiment, the subject device is characterized by a piercing member made of coaxially spaced-apart working and reference electrodes that provide for an electrochemical reaction cell, whereby a reaction area or zone is between the electrodes. The electrochemical cell is employed to make an electrochemical measurement of an analyte in a sample of biological fluid that has been accessed by the piercing member and transported into the electrochemical cell. A porous material is positioned in the space between the electrodes to define the reaction area or zone, that acts to optimally position the electrodes with respect to each other, usually in a parallel configuration. The porous material comprises a plurality of pores that exert a capillary action on the sampled fluid, causing the fluid to be drawn into the porous material.

An exemplary method of the subject invention involves using at least one subject micro-needle having an open distal end and an electrochemical cell therein. The electrochemical cell may further include a redox reagent system and a concentrically-layered electrode configuration, e.g., coaxially working and reference electrodes. The micro-needle is inserted into the skin to a selected depth, preferably to a depth that avoids contacting nerve endings and blood vessels. Next, the sample of biological fluid present at the open distal end of the micro-needle is then wicked, by means of a capillary force, into the electrochemical cell. An electrochemical measurement is then made between the working and reference electrodes, where such a measurement provides an electrical signal that is representative of the concentration the constituent in the sample. The concentration of the constituent in the patient's blood is then derived from the obtained electrical signal. A numerical value representing this concentration may then be displayed on a display unit. A software algorithm that is part of the device, e.g., programmed into the control unit present in the device, may be employed to determine the signal levels transmitted by the control unit to the cell and for deriving the concentration level of the target analyte.

In some embodiments, the subject invention includes a system characterized by one or more devices, each in the form of a micro-piercing member, a control unit, a display unit and a housing. Also provided by the subject inventions are kits for use in practicing the methods of the subject invention.

The subject devices, systems, methods and kits find use in analyte concentration measurement of a variety of analytes and are particularly suited for use in the measurement of glucose concentration in interstitial fluid.

BRIEF DESCRIPTION OF THE DRAWINGS

FIG. 1 includes FIGS. 1A, 1B, 1C and 1D wherein

DETAILED DESCRIPTION OF THE PREFERRED EMBODIMENTS

Figure 1A:
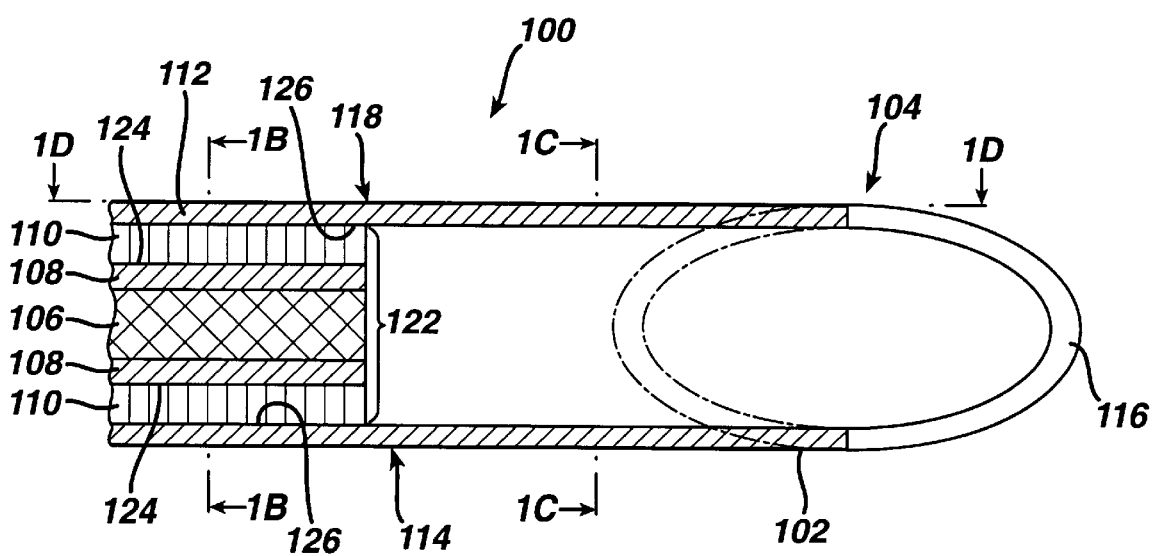
FIG. 1A is a partial cut-away view of a length of a micro-needle of the present invention.

Percutaneous devices and systems, as well as methods for using the same are provided by the subject invention. A feature of the subject devices is the presence of a piercing member that includes concentric working and reference electrodes that define an electrochemical cell having a reaction area or zone into which accessed fluid flows and with which an electrochemical measurement of an analyte present in accessed fluid present therein is made. The present invention finds use in the sampling of biological fluids such as blood, blood fractions, interstitial fluid and the like, and in the detection and measurement of a variety of different analytes, e.g., glucose, cholesterol, electrolytes, pharmaceuticals, illicit drugs, and the like. In further describing the subject invention, a general overview is first provided. The subject devices, systems and methods for their use are discussed in greater detail, followed by a review of the subject kits.

Before the present invention is described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a test strip" includes a plurality of such test strips and reference to "the processor" includes reference to one or more processors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

GENERAL OVERVIEW

The devices of the subject invention generally include a skin-penetration means, a fluid sampling means and a constituent measurement means, in many embodiments integrated into a single structure. The skin-penetration means has at least one micro-piercing member, e.g., a micro-needle or the like, used to penetrate the skin to a depth where pain and bleeding are minimized, and preferably non-existent. Thus, in many embodiments, the micro-needle penetrates above the level where nerves are present. As such, target skin layers into which the subject piercing members may extend to include the dermis, epidermis and the stratum corneum (i.e., the outermost layer of the epidermis).

The devices further include a fluid sampling means, where such fluid sampling means is provided by the construct and geometry of the micro-needle itself, and more particularly, its internal construct and geometry. Specifically, the micro-needle has a generally elongated shape and an open distal tip extending into a space or spaces within its structure that are small enough to create a capillary force on fluid present at the open distal tip. The capillary force acts to access or draw the fluid (e.g., interstitial fluid and/or blood if so desired and depending on the length of the micro-needle) into a space within the micro-needle and then positions the sampled fluid to be measured by a measurement means.

As mentioned above, a feature of the subject devices is a constituent measurement means. The constituent measurement means of the subject invention is made up of an electrochemical cell formed within the structure of the micro-needle to measure the concentration of a constituent, e.g., an analyte, within the fluid sample. The electrochemical cell includes an electrode arrangement of a working electrode and a reference electrode that provides an input reference signal to the sampled fluid and an output signal representing the concentration of the target constituent or analyte in the sampled fluid. Various electrochemical systems may be employed by the present invention, including systems that are amperometric (i.e., measures current), coulometric (i.e., measures electrical charge) or potentiometric (i.e., measures voltage). These types of electrochemical measurement systems are well known to those of skill in the art. See e.g., U.S. Pat. Nos.: 4,224,125; 4,545,382; and 5,266,179; as well as WO 97/18465 and WO 99/49307, the disclosures of which are herein incorporated by reference.

In many embodiments, the biological fluid sampling and analyte concentration measurements devices, e.g., micro-needles, of the invention each comprise at least two electrodes, a reference electrode and a working electrode. The reference electrode provides the input signal to the electrochemical cell and the working electrode provides the output measurement signal from the cell. In certain embodiments, the electrodes are separated by a porous insulator that defines a reaction zone within the micro-needle, where such a porous insulator acts to optimally position the electrodes with respect to each other. Additionally, the porous insulator acts as a component of the sampling means by providing a capillary-type wicking action or the like sufficient to move or draw sampled fluid into the electrochemical cell.

In certain embodiments, the subject micro-needle includes a redox reagent system, typically on the reactive surface of one or both electrodes. Alternatively, the redox reagent system may be contained within the porous insulator. In either case, the redox reagent system typically comprises one or more enzymes and a mediator.

In the subject invention, the electrochemical cell is in electrical communication with a control means that sets the input reference signal transmitted to the electrochemical cell, receives an output signal from the electrochemical cell and then derives the concentration level of the constituent within the sample from the output signal. In other words, the working and references electrodes are in electrical communication with a means for making an electrochemical measurement using the working and reference electrodes, e.g., a means for applying an electrical current between the two electrodes, measuring a change in the current over time and relating the observed change in current to the concentration of analyte present in the electrochemical cell. The detection and/or concentration of a constituent or analyte in a patient's or user's biological fluid, e.g., blood, is then derived from the concentration level in the fluid sample, the numerical value of which may then be displayed to the patient or user on a display unit.

In many embodiments, the control and display units are integrally housed within a low-profile housing. The housing may take a form that also provides a means of securing or holding one or more micro-needles in a position and arrangement suitable for the particular sampling and measuring application at hand.

As is apparent from the above discussion, the geometry and construct of the subject device provides three functions in a single micro-needle structure: penetration into the skin, collection of a sample of biological fluid and measurement of a constituent or analyte in that sample. In many embodiments, the collection and measurement steps are performed completely in-situ, obviating the conventional techniques of withdrawing a sample from the skin, placing the sample on a reagent test strip, or the like, and using a separate piece of equipment or means to test the sample. Thus, in-situ detection minimizes the lag time associated with obtaining measurement readings of a sample compared to previous diagnostic methods that rely on first extracting biological fluid before the measurement can take place.

SKIN-PENETRATION MEANS

As summarized above, a feature of the subject invention is a skin-penetration means having at least one micro-piercing member, e.g., a micro-needle or the like. Furthermore, an aspect of the present invention is that it eliminates or at least greatly minimizes the pain and bleeding suffered by a patient during the sampling process. Accordingly, the penetration lengths and diameters of the micro-needles must be within certain ranges to accomplish this goal. Of course, those values will vary depending on the type of biological fluid (e.g., interstitial fluid, blood or both) desired for sampling, the skin layer to be accessed and the thickness of the skin layers of the particular patient or device user being tested.

By way of background, the skin includes three distinct layers, a top layer called the epidermis, a middle layer called the dermis and a bottom layer called the subcutaneous layer. The epidermis is about 60 to 120 $\mu$m (microns) thick and comprises four distinct layers: a 10 to 20 $\mu$m outer layer, called the stratum corneum, followed by the stratum granulosum, stratum malpighii and stratum germinativum. The stratum corneum contains cells filled with bundles of cross-linked keratin and keratohyalin surrounded by an extracellular matrix of lipids. The inner three layers are collectively referred to as the viable epidermis and have a total thickness in the range of about 50 to 100 $\mu$m. The viable epidermis is responsible for diffusing metabolites to and from the dermis. The epidermis contains no blood cells or nerve endings. The dermis is much thicker than the epidermis, having a thickness in the range from about 2,000 to 3,000 $\mu$m. The dermal layer generally consists of a dense bed of connective tissue, including collagen fibers, and interstitial fluid dispersed throughout these fibers. Below the dermal layer is the subcutaneous tissue that contains the blood capillaries and the majority of nerve endings within the skin.

Thus, in many embodiments, the micro-needles of the present invention may have lengths that extend no deeper than stratum corneum, the epidermis or the dermis layer when fully penetrated into the skin to minimize the pain felt by the patient; however, they may be longer if necessary for the particular sampling application at hand. Also, the length-to-diameter aspect ratio of the micro-needle is important in determining an optimal length for the subject micro-needles. Accordingly, in order to effectively and atraumatically penetrate the skin, the length of the micro-needle is usually at least about 5 times greater than the diameter of the micro-needle, but may be more or less. As will be further described below, the minimum micro-needle diameter is dependent upon the necessary spacing between the electrodes and the diameters of the other components of the electrochemical cell. Thus, the subject micro-needles generally have a length in the range from about 500 to 4,000 $\mu$m, typically between about 600 to 3,000 $\mu$m, and more typically between about 1,000 to 2,000 $\mu$m; however, these lengths will vary from patient to patient depending on the various factors as noted above, and on the thickness of the skin layers of the particular patient being tested. It will be apparent to one of skill in the art that while the micro-needles of the subject invention may have lengths that are longer than the depth of the target skin layer, the micro-needle may be penetrated into the skin at a depth (referred to as the penetration length) that is less than the length of the micro-needle structure. Thus, in order to minimize pain to the patient, the micro-needles in many embodiments have a penetration length in the range from about 50 to 4,000 $\mu$m, and more typically from about 100 to 3,000 $\mu$m. For example, for sampling applications which require penetration only into the epidermis layer, the penetration length of the micro-needle is typically between about 50 to 120 $\mu$m. For sampling applications which require penetration into but no deeper than the dermis layer, the penetration length of the micro-needle is typically from about 2,000 to 3,000 $\mu$m.

The general configuration of an exemplary micro-needle of the present invention will now be described with reference to FIGS. 1A–D. Micro-needle 100 has a configuration that is substantially straight along the longitudinal axis and has a substantially circular cross-section. However, any suitable cross-sectional configuration may be employed including, but not limited to, other annular shapes such as elliptical and oblong, or polygonal configurations, such as square and rectangular. The outer diameter of a micro-needle at its thickest point typically does not exceed about 350 $\mu$m and is usually between about 200 $\mu$m to 300 $\mu$m. In certain embodiments the outer diameter is typically about 250 $\mu$m.

Figure 1B:
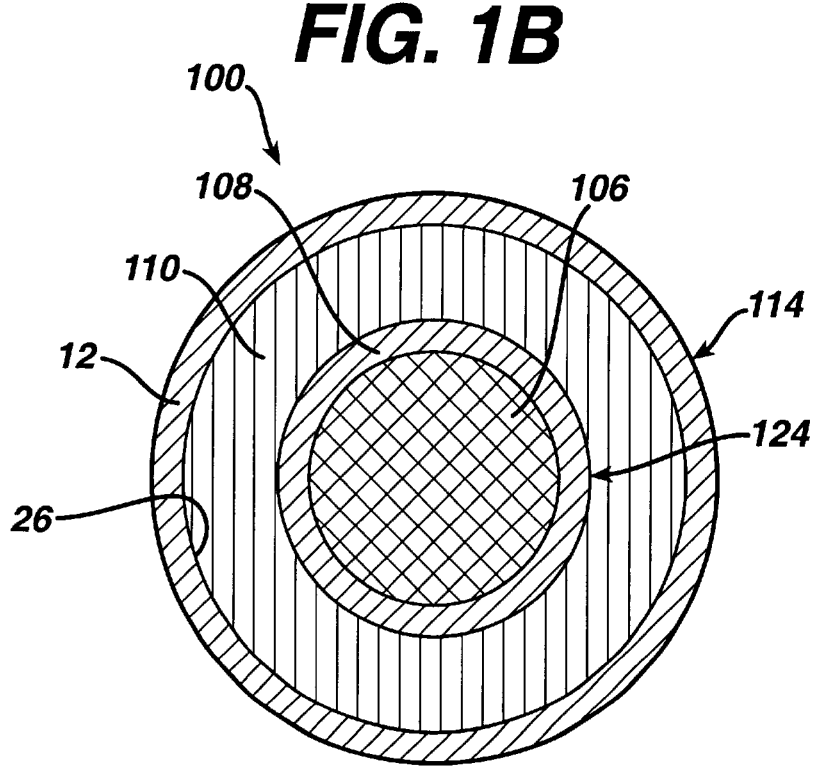
FIG. 1B is a cross-sectional view of the micro-needle of FIG. 1A along the arrows b—b.
Figure 1C:
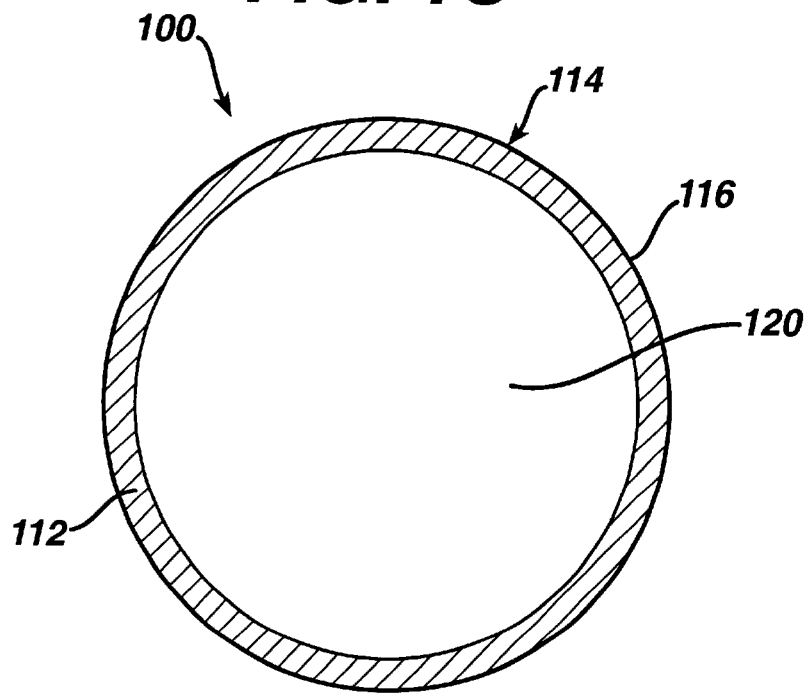
FIG. 1C is a cross-sectional view of the micro-needle of FIG. 1A along the arrows c—c and FIG. 1D is a top view of the micro-needle of FIG. 1A along the arrows d—d.
Figure 1D:
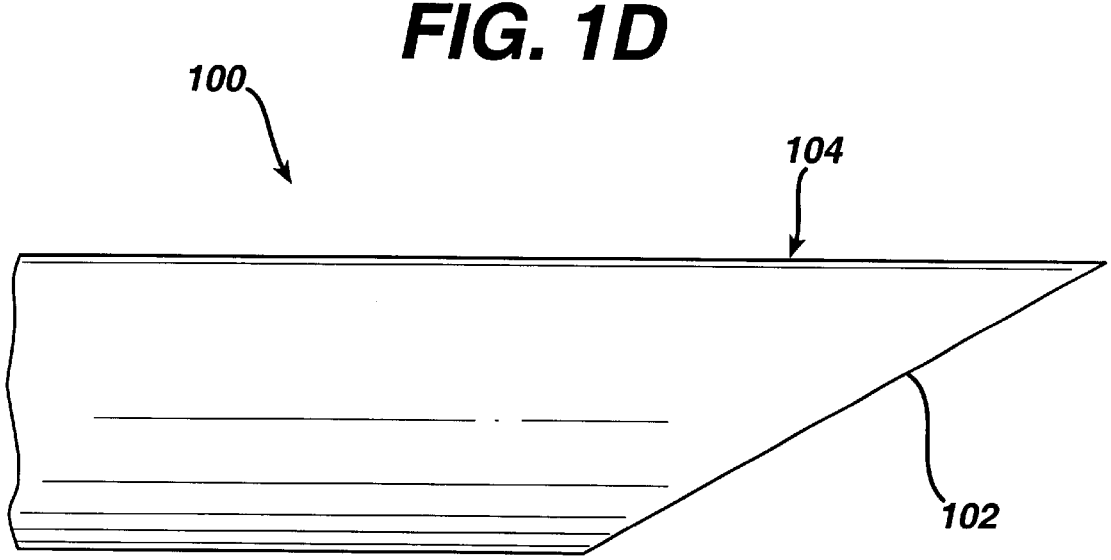

Micro-needle 100 terminates at distal end 104, in preferably a sharp tip 102 having a beveled or sliced configuration, as shown in FIG. 1D, to more easily penetrate the skin. However, tip 102 may have other suitable configurations such as one that is not tapered and defines an edge that lies in a plane perpendicular to the longitudinal axis of the micro-needle (not shown).

Any suitable number of micro-needles, in the form of an array, may be employed by the present invention. The number of micro-needles employed will depend upon various factors including the agent being detected, the body surface location into which the micro-needles are inserted, the sample site, the fluid volume and the like. The micro-needle array may include micro-needles having varying shapes, lengths, widths and tip configurations.

ELECTROCHEMICAL CELL

As discussed above, a feature of the subject invention is the presence, in the piercing means, of an electrochemical cell that is defined by concentric working and reference electrodes. Micro-needle 100 includes an electrochemical cell that provides an electrical signal or signals representative of the concentration of the analyte being measured in a sampled biological fluid. The electrochemical cell comprises various components or layers arranged concentrically with respect to each other. In many embodiments, this concentric arrangement may also be circumferential or co-axial.

Viewed longitudinally in FIG. 1A and in cross-section in FIG. 1B, micro-needle 100 includes, a solid wire core 106 and an outer plating 114. The solid wire core 106 provides rigidity to the micro-needle structure and may be part of the adjacent electrode. The outer plating 114 may be made of stainless steel or the like. Between wire core 106 and outer plating 114 resides the subject electrochemical cell, which includes, from inside out, a first or inner electrode 108, a porous insulator 110 and a second or outer electrode 112.

As shown in the proximal to distal end view of FIG. 1C taken along arrows c—c of FIG. 1A, second or outer electrode 112 and outer plating 114 extend to define edge 116 and tip 102 of micro-needle 100. The three innermost layers, insulator 110, first electrode 108 and solid wire core 106, extend evenly to a location or area 118 (proximal to distal end 104), wherein these three layers have distal edges that are substantially flush with each other. These flush edges define the closed proximal end 122 of a lumen portion 120 having a lumenal wall, defined by second electrode 112 and outer plating 114, which extends to a distal opening at distal edge 116, as viewed in FIG. 1A. Lumen 120 acts to create a capillary force which wicks biological fluid present into lumen opening 128 at tip 102. Lumen 120 has a volume which does not exceed about 250 nL and is generally in the range from about 20 to 140 nL. In certain embodiments the volume is typically about 65 nL. Porous insulator 110 then provides a secondary capillary force to wick an amount of the biological fluid contained within lumen 120 into itself.

Solid wire core 106 has a diameter which typically does not exceed about 120 $\mu$m, and more typically is in the general range from about 80 to 100 $\mu$m. In certain embodiments the diameter is typically about 90 $\mu$m. First electrode 108 has a cylindrical configuration (although other configurations are possible) having a thickness which typically does not exceed about 300Å, and more typically is in the general range from about 70 to 200Å. In certain embodiments the thickness is typically about 100Å. Porous insulator 110 also has a cylindrical configuration (although other configurations are possible) having a thickness which typically does not exceed about 200 $\mu$m, and more typically is in the general range from about 50 to 80 $\mu$m. Second electrode 112 also has a cylindrical configuration (although other configurations are possible) having a thickness which typically does not exceed about 300Å and more typically is in the general range from about 70 to 200Å. The thin outer tube 114 upon which the second electrode 112 is electroplated has a thickness which typically does not exceed about 25 $\mu$m and more typically is in the general range from about 12 to 20 $\mu$m.

The electrode 112, i.e., the outer electrode, is used as the reference electrode, i.e., the electrode which provides an input signal to the electrochemical cell, and the other electrode 108, i.e., the inner electrode, is employed as a working electrode, i.e., the electrode which provides an output signal representative of the analyte concentration within the sampled fluid. Typically, the length of the outer electrode is the same as the length of the micro-needle, and thus is generally not greater than about 4,000 $\mu$m. More typically, the length of the outer electrode is between about 1,000 $\mu$m to 3,000 $\mu$m, and usually is about 2,000 $\mu$m. The inner electrode may have the same length as the outer electrode, but may often times be shorter than the outer electrode. The length of the inner electrode is generally about 20% shorter than the outer electrode and is generally not greater than about 3,200 $\mu$m, and is typically between about 800 to 2,400 $\mu$m, and is more typically about 1,600 $\mu$m.

At least the surfaces of the electrodes that face the reaction zone (i.e., the porous insulator) within the micro-needle are made of highly conductive metal, such as palladium, gold, platinum, silver, iridium, carbon, doped indium tin oxide, stainless steel and the like, or a combination of such materials. Most typically the metal is gold, platinum or palladium. Although the entire electrode may be made of metal, each electrode may be made up of an inert support or backing substrate, on the surface of which is a thin layer of the metal component (e.g., an electroplated metal layer) of the electrode.

POROUS INSULATOR

As mentioned above, the working and reference electrodes define the boundaries of the reaction zone that, in the embodiment of FIG. 1, is in the form of a cylindrical donut, for example. The reaction zone is filled with a hydrophilic porous insulator having an inner and an outer surface area and having a thickness that typically does not exceed 150 $\mu$m and generally is in the range from about 50 to 80 $\mu$m. The volume of the reaction zone typically does not exceed about 150 nL and is generally from about 15 to 110 nL. In certain embodiments the volume is typically about 50 nL.

The porous insulator comprises pores or voids throughout at least a portion of the micro-needle structure. The pores are sufficiently sized to provide a capillary force so as to wick in fluid from lumen 120. The pores are also sufficiently interconnected to permit passage of or conduction of a fluid through the porous material. The average pore size is from about 1000 to 5000 nm and more typically about 1000 to 2000 nm. The porous insulator may be made of ceramics or plastic materials such as polymers. Suitable types of polymer materials include, but are not limited to, polyimides, polysulfone, and cellulosic. As is well known in the art, polymers may be rendered porous by removing leachable or volatizable material contained therein.

REAGENTS

A redox reagent(s) system is typically employed to single out and sense the target analyte or constituent selected to be analyzed over the other constituents in the sampled biological fluid. The redox reagent(s) of the redox reagent system may reside on the reactive surface, i.e., the surface facing the porous insulator, of one or both electrodes, but in many embodiments the redox reagent(s) will reside on the reactive surface of the working electrode. As such, the reagent is often times coated or deposited on the surface(s) by means of dip coating, where such processes are well known in the art. Alternatively, the reagent may be contained within the porous insulator by saturation coating, as is known in the art. The reagent system used is selected based on the analyte targeted for detection. The interaction of the reagent system and the corresponding constituent or analyte determines the concentration of the target analyte or constituent in the cell.

The reagent system present in the reaction area typically includes at least an enzyme(s) and a mediator. In many embodiments, the enzyme member(s) of the reagent system is an enzyme or a plurality of enzymes that work in concert to oxidize the analyte of interest. In other words, the enzyme component of the reagent system is made up of a single analyte oxidizing enzyme or a collection of two or more enzymes that work in concert to oxidize the analyte of interest. Enzymes of interest include oxidases, dehydrogenases, lipases, kinases, diaphorases, quinoproteins and the like. The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the reagent system is a glucose-oxidizing enzyme (e.g., a glucose oxidase or glucose dehydrogenase).

As described above, the reagent system may further include a second component, i.e., a mediator component, which is made up of one or more mediator agents. A variety of different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes and the like. In those embodiments where glucose in the analyte of interest and glucose oxidase or glucose dehydrogenase is the enzyme components, mediator of particular interest is ferricyanide. Other reagents that may be present in the reaction area include buffering agents, (e.g., citraconate, citrate, phosphate), "Good" buffers and the like.

The reagent(s) is generally present in dry form. The amounts of the various components may vary, wherein the amount of enzyme component typically ranges from about 0.1 to 10% by weight.

EXEMPLARY EMBODIMENT OF SYSTEM

As described above, the subject invention includes a system for sampling biological fluid from the skin of a patient or user and measuring a target constituent within the biological fluid, where such a system generally is made of at least one micro-needle having a sampling means, a reagent and an electrochemical cell, as described above, and a control unit having means for sending and receiving electrical signals and a software algorithm.

Figure 2:
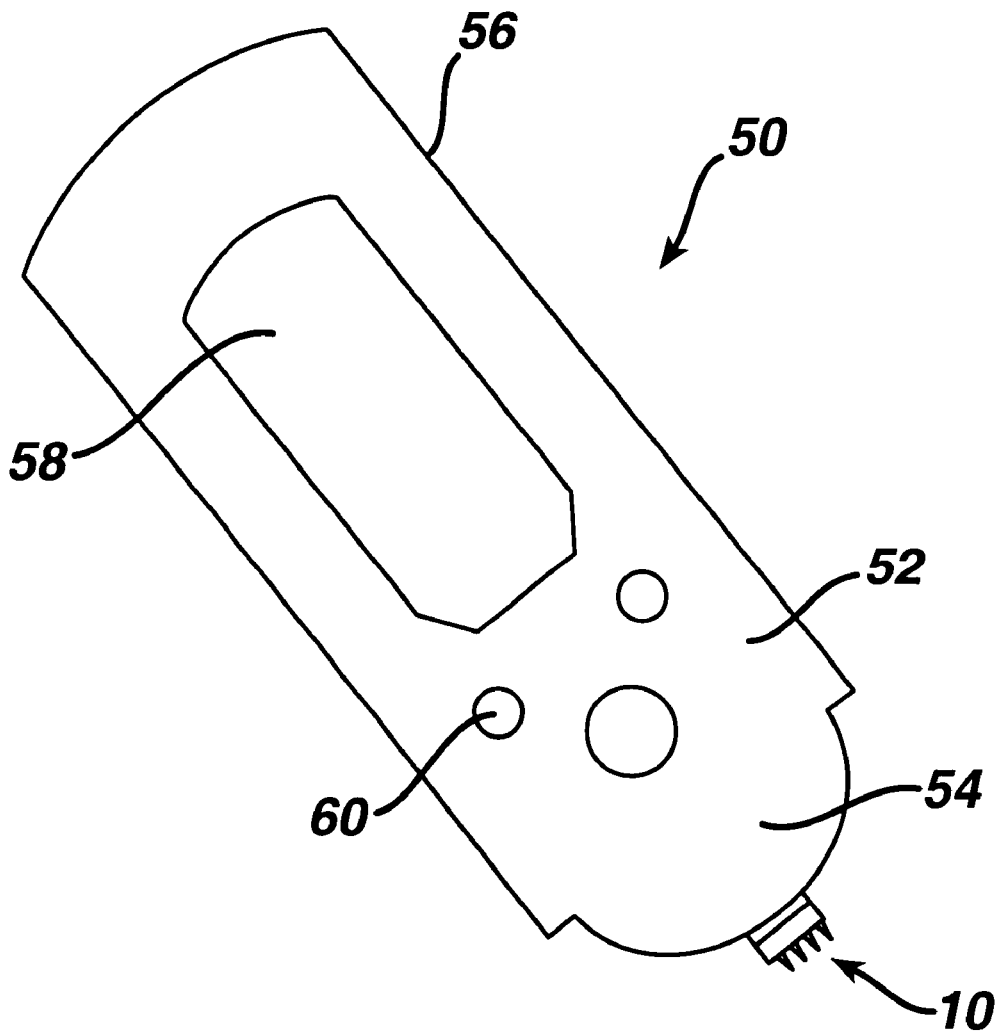
FIG. 2 is a schematic representation of the sampling and measurement device of the present invention.

Referring now to FIG. 2, there is shown a schematic representation of an exemplary system 50 of the subject invention. System 50 includes a hand-held control unit 52 and a device 10, as described above, operatively mounted to distal end 54 of control unit 52. Device 10 includes an array of the micro-needles of the present invention, such as micro-needle 100 of FIG. 1. Control unit 52 has a housing 56, typically made of a medical grade plastic material, having a low-profile configuration which houses a means (not shown) for controlling the measurement means of device 10, i.e., generating and transmitting input reference signals to the electrochemical cell of micro-needle 100 and receiving output measurement signals from the cell. Housing 56 may further include a means for supporting the micro-needle array or a single micro-needle, such as a support or substrate or the like (not shown).

A software algorithm programmed within control unit 52 automatically calculates and determines the concentration of the target analyte in the biological sample upon receipt of the output signal. The concentration level (among other desired information) is then transmitted to an external display means or screen 58 that displays information to the user. Control interface buttons 60 are provided to allow the user to input information to the control means, such as the type of analyte targeted for measurement.

Device 10 is electrically and physically coupled to control unit 52. Electrical communication between the two is established by means of conductive contacts (not shown) on device 10 and corresponding electrical traces (not shown) within control unit 52. In certain embodiments, device 10 and control unit 52 are physically coupled by a quick lock-and-release mechanism (many of which are commonly known) such that a used device can be easily removed and replaced. Control unit 52 is typically reusable and usable with any number of devices of the subject invention. These features facilitate the taking of multiple samples and measurements in an efficient and rapid manner.

METHODS OF USE

Also provided by the subject invention are methods for using the subject devices and systems to determine the concentration of an analyte in a biological sample. A variety of different analytes may be detected using the subject devices and systems, where representative analytes include, but are not limited to, glucose, cholesterol, lactate, alcohol, electrolytes, pharmaceuticals, illicit drugs, and the like.

In practicing the subject methods (with reference to the Figures), the first step is to provide a device 10 having one or more micro-needles 100 of the present invention. In many embodiments, device 10 is particularly configured (i.e., device 10 includes the appropriate reagent(s)) for targeting the analyte(s) of interest. The device 10 is operatively engaged and interfaced with a control unit 52 that can be manually held and controlled by the user. Control unit 52 is programmed for testing the targeted analyte(s). The device 10 is positioned over a selected area of the user's skin, and, with slight pressure, the array of micro-needles 100 of device 10 are caused to penetrate into the skin. The depth to which the micro-needles 12 are inserted will depend on the length of the respective micro-needles or by some other means associated with the device 10 for limiting the insertion depth.

Upon insertion into the user's skin, an amount (i.e., a sample) of biological fluid present at the open tips 102 of micro-needles 100 is caused to wick into lumens 120 of the respective micro-needles by means of a capillary force, i.e., most or all of the biological fluid is transferred in situ into the device 10. The porous insulator 110 continues to wick the fluid into the reaction zone of the electrochemical cell by means of a capillary force.

As discussed above, micro-needle 100 may be manufactured with a selected redox reagent system placed on opposing surfaces 124 and 126 of first electrode 108 and second electrode 112, respectively, or alternatively, the reagent is infused within porous insulator 110. The type of reagent system is selected based on the type of analyte targeted for measurement. Thus, when the sample of biological fluid is absorbed into the porous insulator 110, the targeted analyte within the sample chemically reacts with the reagent, causing the analyte to oxidize. This chemical reaction creates a change in the impedance (or resistance) level across the reaction zone within the electrochemical cell.

More specifically, once in the reaction zone, the targeted analyte chemically reacts with the selected reagent(s) to form electroactive products. The electroactive products are then either oxidized or reduced by the optional mediator or directly by the working electrode 108. The resulting output signal level is then conducted to the control unit by electrode 108. A software algorithm programmed within control unit 52 then automatically determines the differential between the output and reference signals, derives the concentration of analyte in the sample from this differential value, and then derives the corresponding concentration level of the selected analyte in the patient's blood. Any or all of these values may be displayed by display means or screen 58.

A device such as control unit 52 which automatically calculates and determines the concentration of a selected analyte in a biological sample and/or in the patient's system, such that a user need only insert a micro-needle of the subject invention into the patient's skin and then read the final analyte concentration result from a display of the device, is further described in U.S. Pat. No. 6,193,873 entitled "Sample Detection to Initiate Timing of an Electrochemical Assay," the disclosure of which is herein incorporated by reference.

KITS

Also provided by the subject invention are kits for use in practicing the subject methods. The kits of the subject invention include at least one subject device having one or more micro-needles. The kits may also include a reusable or disposable control unit that may be used with reusable or disposable devices of the kit or from other kits of the subject invention. These kits may include devices having an array of micro-needles having the same or different lengths. Certain kits may include various devices each containing the same or different reagents. Also, more than one reagent may be provided within a single micro-needle array, wherein one or more of the micro-needles are provided with a first reagent for testing a first target analyte and one or more other micro-needles are provided with other reagents for testing other targeted analytes. Finally, in many embodiments, the kits include instructions for using the subject devices in the determination of an analyte concentration in a physiological sample. These instructions may be present on one or more of the packaging, a label insert, or containers present in the kits, and the like.

It is evident from the above description that the subject inventions are easy to use and can provide for analyte testing without the need to cut or lance the skin and with minimal or no pain and blood. As such, the subject invention represents a significant contribution to the field.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

Although the present invention is useful for many applications, the sampling of various biological fluids and the detection of many types of constituents, the invention has been described primarily in the context of the detection of analytes in interstitial fluids, and as being particularly useful for the detection of glucose in interstitial fluid. Thus, the specific devices and methods disclosed and the applications, biological fluids and constituents discussed herein are considered to be illustrative and not restrictive. Modifications that come within the meaning and range of equivalents of the disclosed concepts, such as those that would readily occur to one skilled in the art, are intended to be included within the scope of the appended claims.

What is claimed is:

1. A biological fluid sampling and analyte concentration measurement device, said device comprising:
   (a) an elongated sampling means configured to pierce a skin surface to provide access to the biological fluid; and
   (b) concentrically-spaced electrodes positioned within the elongated sampling means that define an electrochemical cell for measuring the concentration of analyte within the biological fluid.

2. The device of claim 1 further comprising an insulating material between the concentrically-spaced electrodes.

3. The device of claim 2 further comprising a redox reagent system.

4. The device of claim 2 wherein the insulating material comprises a plurality of pores configured to provide a capillary force sufficient to draw a sample of biological fluid into the pores.

5. The device of claim 1 further comprising a signal producing and receiving means in electrical communication with the electrodes.

6. The device of claim 1 wherein the sampling means comprises a lumen and an open distal end, wherein the open distal end provides a passageway into the lumen.

7. The device of claim 6 wherein the lumen is configured to provide a capillary force sufficient to draw a sample of biological fluid into the lumen.

8. The device of claim 1 wherein the biological fluid is interstitial fluid and the analyte is glucose.

9. A kit comprising at least one biological fluid sampling and analyte concentration measurement device according to claim 1.

10. A device for sampling biological fluid and measuring the concentration of a target constituent in the biological fluid, comprising:
    a first electrode;
    a second electrode concentrically positioned about and spaced apart from the first electrode; and
    a porous material positioned in the space between the electrodes, wherein the device has a configuration for piercing the skin.

11. The device according to claim 10 having a penetration length no deeper than the dermis.

12. The device according to claim 11 having a penetration length no deeper than the epidermis.

13. The device according to claim 10 wherein the second electrode has a configuration for piercing the skin.

14. The device according to claim 13 wherein the second electrode has an open distal end and defines a space within the device, wherein the space has a configuration to provide a capillary force sufficient to draw biological fluid through the open distal end.

15. The device according to claim 10 further comprising a reagent in contact with the porous material or at least one of the electrodes.

16. The device according to claim 15 wherein the reagent is located on a surface of at least one of the electrodes facing the porous material.

17. A micro-needle for sampling a biological fluid and measuring a target constituent within the biological fluid, comprising:

a core having a length;

a first electrode coaxially conformed about the core length;

a porous material coaxially conformed about the first electrode;

a second electrode coaxially conformed about the porous material and having a length that extends beyond the core length and terminates at an open tip; and a reagent contained within the micro-needle wherein the reagent is selected based on the target constituent.

18. The micro-needle according to claim 17 further comprises a plating formed circumferentially about the length of the second electrode.

19. A kit for sampling a biological fluid from the skin of a patient and for measuring the concentration of a constituent within the sampled biological fluid, the kit comprising:

at least one micro-needle according to claim 17.

20. The kit according to claim 19 further comprising a plurality of micro-needles and a support member wherein the plurality of micro-needles are arranged in an array on the support member.

21. The kit according to claim 20 wherein the micro-needles have varying lengths.

22. The kit according to claim 20 wherein the micro-needles comprise different reagents.

23. A system for sampling biological fluid from the skin of a patient and measuring a target constituent within the biological fluid, the system comprising:

(a) at least one micro-needle comprising sampling means, a reagent and an electrochemical cell housed within the micro-needle,
 (1) wherein the electrochemical cell comprises a reference electrode, a working electrode and an insulating material there between, wherein the reagent is in contact with at least one or more of the reference electrode, the working electrode or the insulating material, and
 (2) wherein the sampling means comprises a distal opening and at least one space within the micro-needle having a configuration capable of wicking biological fluid into the micro-needle; and (b) a control unit in electrical communication with the at least one micro-needle, comprising:
 (1) means for sending an electrical reference signal to the reference electrode and for receiving an electrical output signal from the working electrode, and
 (2) a software algorithm which automatically calculates and determines the concentration of the target constituent in the biological sample upon receipt of the electrical output signal.

24. The system according to claim 23 further comprising a display unit in electrical communication with the control unit for displaying information in the form of electrical signals received from the control unit related to the sampling of the biological fluid and the measuring of the target constituent.

25. The system according to claim 23 further comprising a housing and a support means wherein the control unit is housed within the housing and the at least one micro-needle is mounted to the support means.

26. A method for testing a biological fluid within the skin of a patient and for determining the concentration of a target constituent contained therein, the method comprising the steps of:

providing at least one micro-needle comprising an open distal end and an electrochemical cell therein, the electrochemical cell comprising a reagent and a concentrically-layered electrode configuration;

inserting the at least one micro-needle into the skin to a selected depth;

wicking a sample of biological fluid present at the open distal end into the electrochemical cell;

allowing the sample to react with the reagent wherein a substance is formed within the electrochemical cell as a result of the reaction;

providing a first electrical signal to the substance; and receiving a second electrical signal generated by the substance, wherein the second electrical signal is representative of the concentration the constituent in the sample.

27. The method according to claim 26 wherein the selected depth is no greater than the viable epidermis.

28. The method according to claim 27 wherein the selected depth is no greater than the stratum corneum.

29. The method according to claim 26 wherein the step of wicking comprises exerting a capillary force on the biological fluid present at the open distal end.

30. The method according to claim 26 wherein the steps of providing a first electrical signal and receiving a second electrical signal is performed by a control unit in electrical communication with the electrochemical cell.

31. The method according to claim 26 further comprising the step of deriving the concentration of the constituent in the patient's blood from the second electrical signal.

32. The method according to claim 31 further comprising the step of displaying a numerical value representative of the concentration of the constituent in the patient's blood.

33. The method according to claim 31 wherein the step of deriving comprises using a software algorithm.

* * * * *